United States Patent [19]
Orr et al.

[11] Patent Number: 5,382,239
[45] Date of Patent: Jan. 17, 1995

[54] REPOSITIONAL CATHETER FIXATION DEVICE

[75] Inventors: Douglas P. Orr, Sandy; Gerald D. Powelson, American Fork; Mark Crawford, Sandy, all of Utah

[73] Assignee: Becton, Dickinson and Company, Franklin Lakes, N.J.

[21] Appl. No.: 873,903

[22] Filed: Apr. 24, 1992

[51] Int. Cl.⁶ ............................................. A61M 5/32
[52] U.S. Cl. ................................................. 604/177
[58] Field of Search ............... 604/177, 178, 179, 180, 604/174, 250

[56] References Cited

U.S. PATENT DOCUMENTS

| | | | |
|---|---|---|---|
| 2,669,231 | 2/1954 | Fisher | 604/179 |
| 2,882,898 | 4/1959 | Holmes . | |
| 3,574,306 | 4/1971 | Alden . | |
| 3,589,361 | 6/1971 | Lopez . | |
| 3,640,275 | 2/1972 | Burke et al. . | |
| 4,129,128 | 12/1978 | McFarlane . | |
| 4,333,468 | 6/1982 | Geist | 604/180 |
| 4,336,806 | 6/1982 | Eldridge, Jr. . | |
| 4,360,025 | 11/1982 | Edwards | 604/180 |
| 4,553,961 | 11/1985 | Pohndorf et al. | 604/175 |
| 4,583,976 | 4/1986 | Ferguson | 604/174 |
| 4,632,670 | 12/1986 | Mueller, Jr. | 604/174 |
| 4,699,616 | 10/1987 | Nowak et al. | 604/180 |
| 4,726,716 | 2/1988 | McGuire | 604/180 |
| 4,838,878 | 6/1989 | Kalt et al. | 604/180 |
| 4,897,082 | 1/1990 | Erskine | 604/180 |
| 4,906,233 | 3/1990 | Moriuchi et al. | 604/174 |
| 4,962,757 | 10/1990 | Stefan . | |
| 4,981,475 | 1/1991 | Haindl | 604/174 |
| 5,026,352 | 6/1991 | Anderson | 604/178 |
| 5,037,397 | 8/1991 | Kalt et al. | 604/174 |

FOREIGN PATENT DOCUMENTS 2643269  8/1990  France ........................ 604/180

Primary Examiner—Gene Mancene
Assistant Examiner—Jeffrey A. Smith
Attorney, Agent, or Firm—Arthur D. Dawson

[57] ABSTRACT

A medical device for securing tubing such as intravenous catheter tubing to a patient. The device is made up of two lobes, each being made up of a channel and a tab. The device is hinged so that the tabs can be brought together. When the tabs are brought together, the tubing is gripped between the gripping channels. The gripping channels have specially adapted surfaces to facilitate the gripping of the tubing. The gripping channels may also be lined with a tacky material or contoured liners.

27 Claims, 6 Drawing Sheets

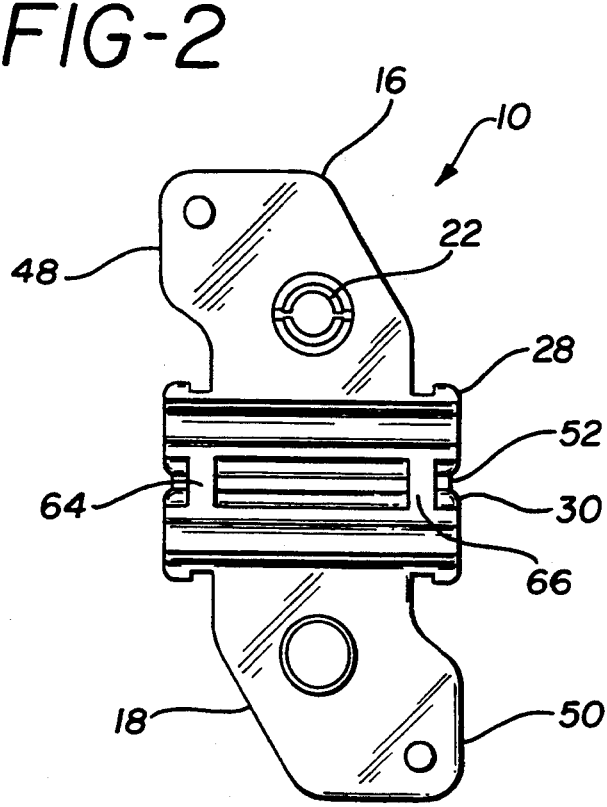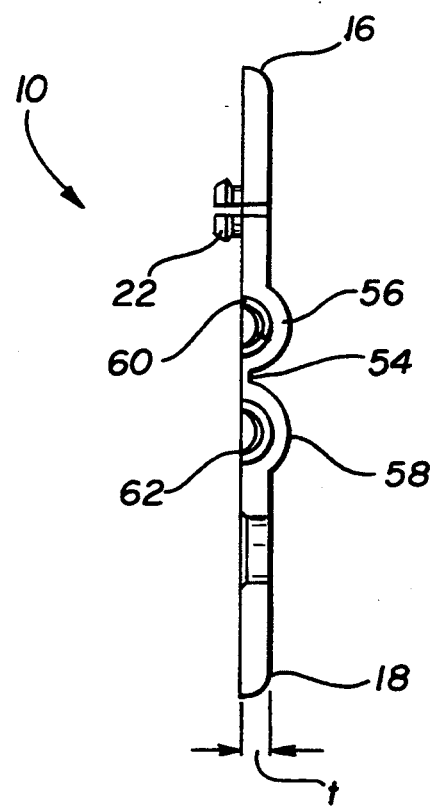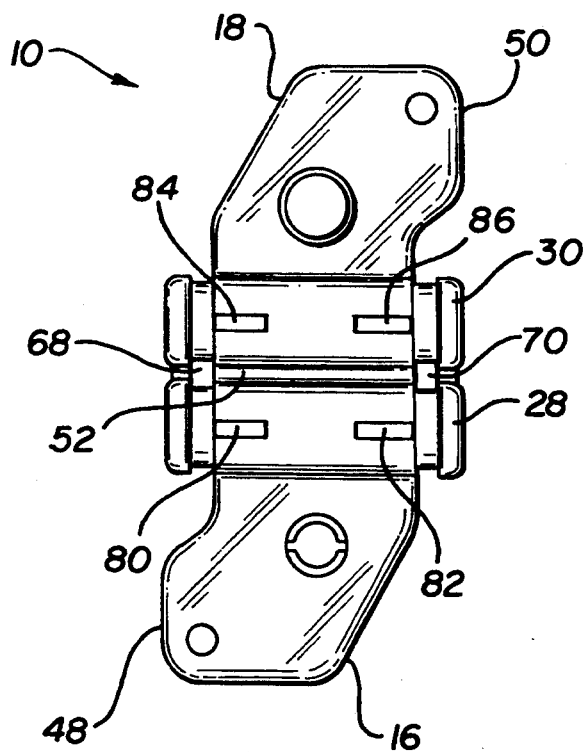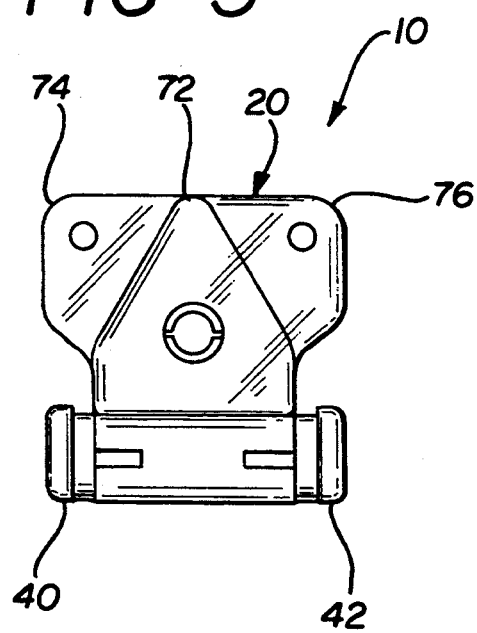

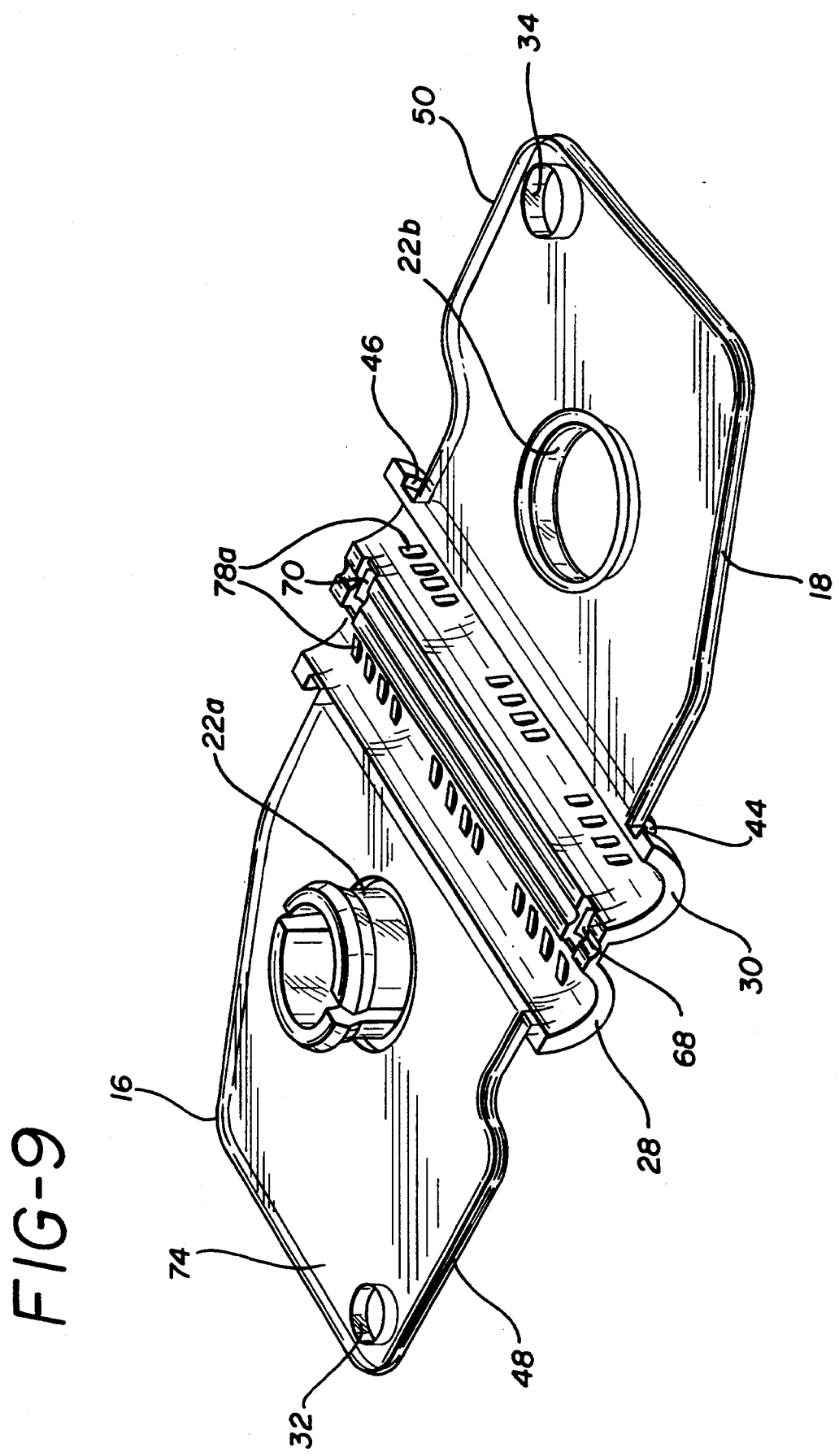

REPOSITIONAL CATHETER FIXATION DEVICE

BACKGROUND OF THE INVENTION

The invention relates to fixation devices for securing tubing such as catheter tubing to a patient undergoing medical treatment.

During medical procedures such as surgery, it is often necessary to infuse medication into a patient or monitor the condition of a patient via tubing such as intravenous catheter tubing. At least part of such tubing lies outside of the patient and must be secured to avoid entanglement or crimping which may impede the infusion or monitoring process.

SUMMARY OF THE INVENTION

The present invention is a device for holding tubing such as intravenous catheter tubing or the like to a patient. The device comprises two lobes. Each of the lobes is made up of a channel and a tab. The inner surface of at least one of the channels is provided with a gripping means which is specially adapted for gripping the tubing. The tubing is gripped between the two channels when the two lobes are brought together and the tabs touch each other. The device is provided with a connector which holds the lobes together so that the channels can grip the tubing.

A hinge is interposed between the two lobes so that the lobes can be rotated about the hinge between an open position and a closed position. When the lobes are brought together, the tabs touch. The tubing is gripped between the channels in the closed position. The tabs are designed so that at least one tab will overlap the other. In order to secure the device to a patient, at least one of the tabs is provided with a suture hole.

The gripping means may have several embodiments. It may have a contoured gripping surface or it may comprise a tacky material which is designed to grip the tubing. The contoured surface may be sinusoidal, roughened uneven or it may be made up of a plurality of bumps. The gripping means may also be made up of a liner which likewise may be made of a tacky material or contoured as described above.

When the lobes are joined, the inside diameter of the tube formed by the channels is typically slightly smaller than the outside diameter of the tubing so that the tubing is gripped by the device without undue constriction. When the lobes are joined a portion of one tab overlaps the other, facilitating suturing and separation of the tabs.

The invention will be further understood by reference to the following drawings and description.

BRIEF DESCRIPTION OF THE DRAWINGS

FIG. 2 is a top view of the preferred embodiment of the invention in its open state;

FIG. 3 is a bottom view of the preferred embodiment of the invention in its open state;

FIG. 4 is a side view of the preferred embodiment of the invention in its open state;

FIG. 5 is a front view of the preferred embodiment of the invention in its closed state;

FIG. 9 is a top perspective view of an alternate embodiment of the invention which does not have a liner.

DETAILED DESCRIPTION

In the following detailed description of the preferred embodiment, reference is made to the accompanying drawings. The description shows by way of illustration a specific preferred embodiment of the invention. This embodiment is described in sufficient detail to enable those skilled in the art to practice the invention. It is to be understood that other embodiments may be utilized and that structural changes may be made without departing from the scope of the present invention. The following detailed description is, therefore, not to be taken in a limiting sense. The scope of the present invention is defined by the appended claims.

Figure 1:
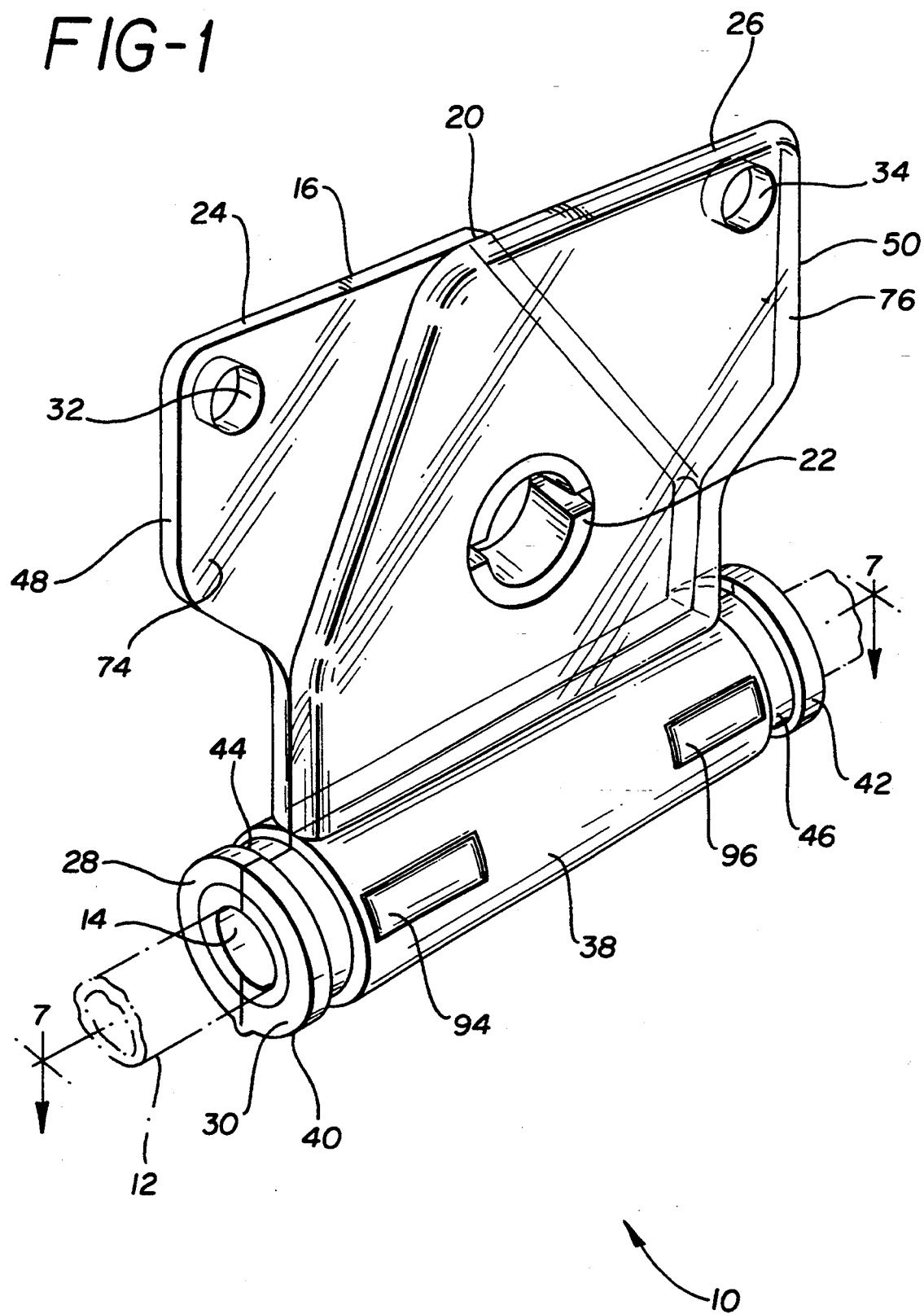
FIG. 1 is a perspective view of the preferred embodiment of the invention in its closed state.
Figure 6:
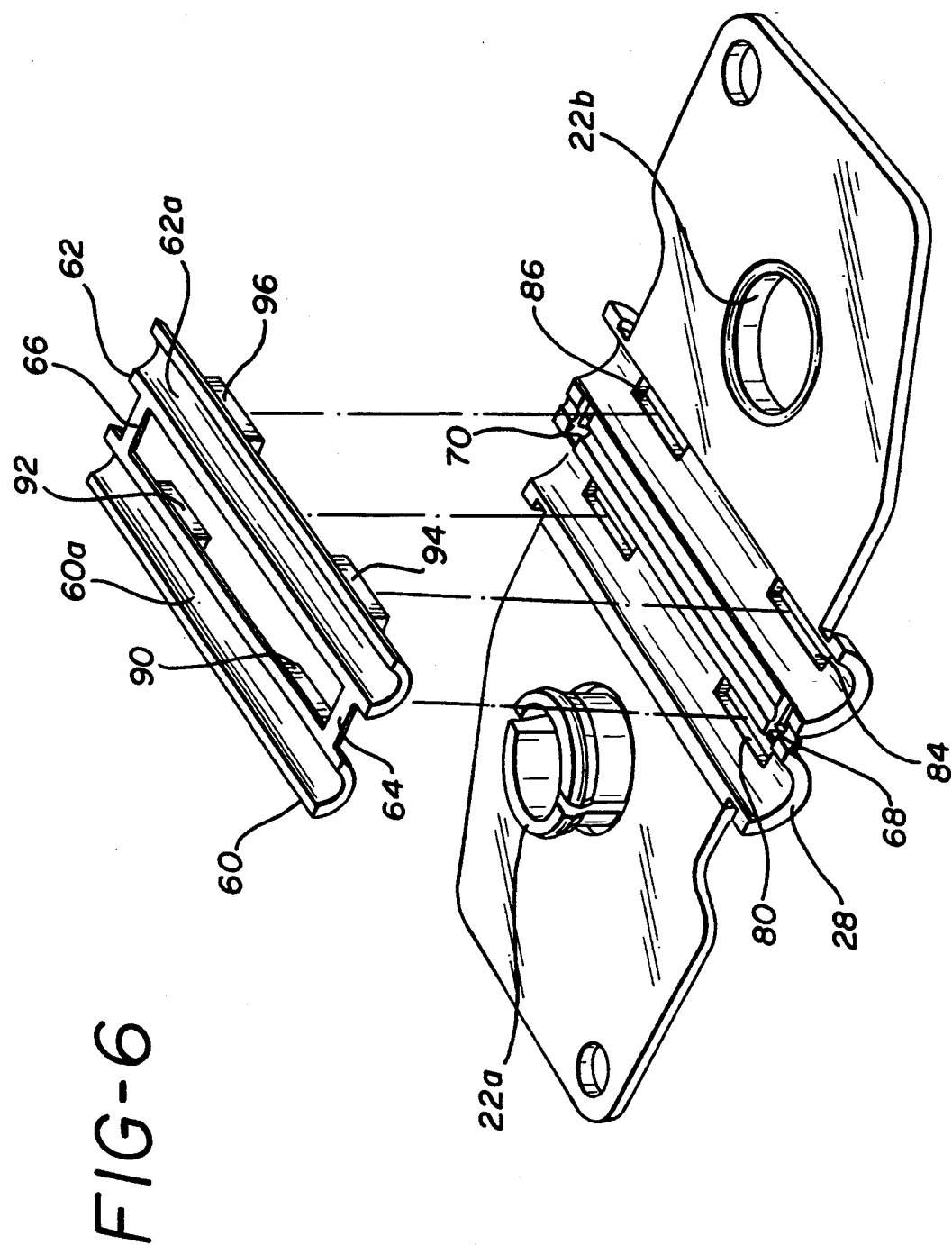
FIG. 6 is a top perspective view of the preferred embodiment of the invention in its open state, showing the liner removed.

FIG. 1 is a perspective view of fixation device 10 in its closed state showing tubing 12 passing through tube gripping lumen 14. The two lobes 16, 18 of fixation device 10 are clipped together by means of snap-connector 22 to form fin 20. Lobes 16 and 18 are preferably made of polypropylene. The preferred grade is PF091B supplied by Himont USA, Inc. However, any polypropylene which is suitable for forming a hinge between lobes 16 and 18 may be used. Lobes 16 and 18 comprise tabs 24 and 26 respectively and semi-cylindrical channels 28 and 30 respectively. Suture holes 32 and 34 are provided in tabs 24 and 26 respectively. Channels 28 and 30 form a generally cylindrical tube holder 38 having a tube gripping lumen 14, a first end 40 and a second end 42. Ends 40 and 42 protrude slightly outwards of fin 20.

Grooves 44 and 46 are provided in end portions 40 and 42 respectively. Grooves 44 and 46 may be used to hold fastener 10 to the skin by means of sutures. Tabs 24 and 26 are provided with overlap portions 48 and 50 respectively. These provide leverage to facilitate the disengagement of snap-fit connector 22, as well as providing a reduced thickness (in comparison with thickness of fin 20) to facilitate the suturing of fin 20 to the skin.

FIGS. 2, 3, 4 and 6 show the fastener 10 in its open state. Lobes 16 and 18 are joined by hinge 52 at the meeting edge 54 of grippers 28 and 30. Lobes 16 and 18 are thus rotatable through about 270° about hinge 52. Hinge 52 is formed during the moulding of lobes 16 and 18 and is made up of a thin web-like section of material joining lobes 16 and 18.

In the preferred embodiment shown in FIGS. 1–7 grippers 28 and 30 comprise outer semi-cylinders 56 and 58 respectively and are lined with liners 60 and 62 respectively. Any soft, easily moldable TPE or silicone could also be used. Liners 60 and 62 provide a surface of relatively high friction to facilitate the gripping of tubing 12. Liners 60 and 62 are hinged by webs 64 and 66 (see FIG. 6) which mate respectively gaps 68 and 70 in hinge 52. Gaps 68 and 70 coincide with grooves 44 and 46 respectively. The radius of liners 60 and 62 is slightly smaller than the outside radius of the tube to be fastened so that the tube 12 will be securely gripped. It will be noted that each gripper is formed with a segment of each of grooves 44 and 46 so that when the fixation device 10 is closed the segments of those grooves form circumferential grooves 44 and 46.

In order to locate liners 60 and 62 in grippers 28 and 30, grippers 28 and 30 are provided with slots 80, 82, 84 and 86. Liners 60 and 62 are respectively provided with projections 90, 92, 94 and 96 which fit tightly into slots 80, 82, 84 and 86 respectively (See FIG. 6).

Tab 24 is provided with male snap connector 22a and Tab 26 is provided with female snap connector 22b. When fixation device 10 is closed, connectors 22a and 22b mate releasably and hold tabs 24 and 26 together securely so that tube 12 is gripped by grippers 28 and 30.

While many shapes are possible for tabs 24 and 26, each is preferably a reverse mirror image of the other. This means that when lobes 16 and 18 are brought together and fixation device 10 is in its closed state, there will be a region 72 of fin 20 in which its thickness is 2t and two regions of overlap 74 and 76 where its thickness is t, (where t is the thickness of each of tabs 24 and 26). Suture holes 32 and 34 are placed in tabs 24 and 26 respectively in regions of overlap 74 and 76 to facilitate the disengagement of snap connector 22. These regions can be gripped easily and provide leverage to make it easy to disengage snap connector 22. Another purpose of these regions of overlap is to provide a thin tab to facilitate the suturing of fastener 10 to the skin.

The inner surfaces 60a and 62a of liners 60 and 62 are specially adapted to facilitate the gripping of tubing 12. There are several ways in which this may be achieved. In the preferred embodiment the inner surfaces 60a and 62a of liners 60 and 62 comprise a tacky or clingy material having a thickness preferably varying between 0.019" and 0.088" but not less than 0.010". The liner material is selected for its compatibility with tubing 12. The tacky material must be such that the coefficient of friction of tubing 12 and liners 60 and 62 is high. This allows tubing to be removed easily on opening of fastener 10 if it is necessary, and increases the gripping ability of grippers 28 and 30. The high coefficient of friction between the liners and the tube makes it difficult to pull the tube through fastener 10 when it is in its closed state. Liners 60 and 62 are preferably made of thermoplastic elastomer (TPE), preferably C-Flex 35-A resin, a styrene-block copolymer (comprising polydimethylsiloxane modifiers) available from Concept Polymer Technologies, Inc. of Clearwater, Fla.

Figure 7:
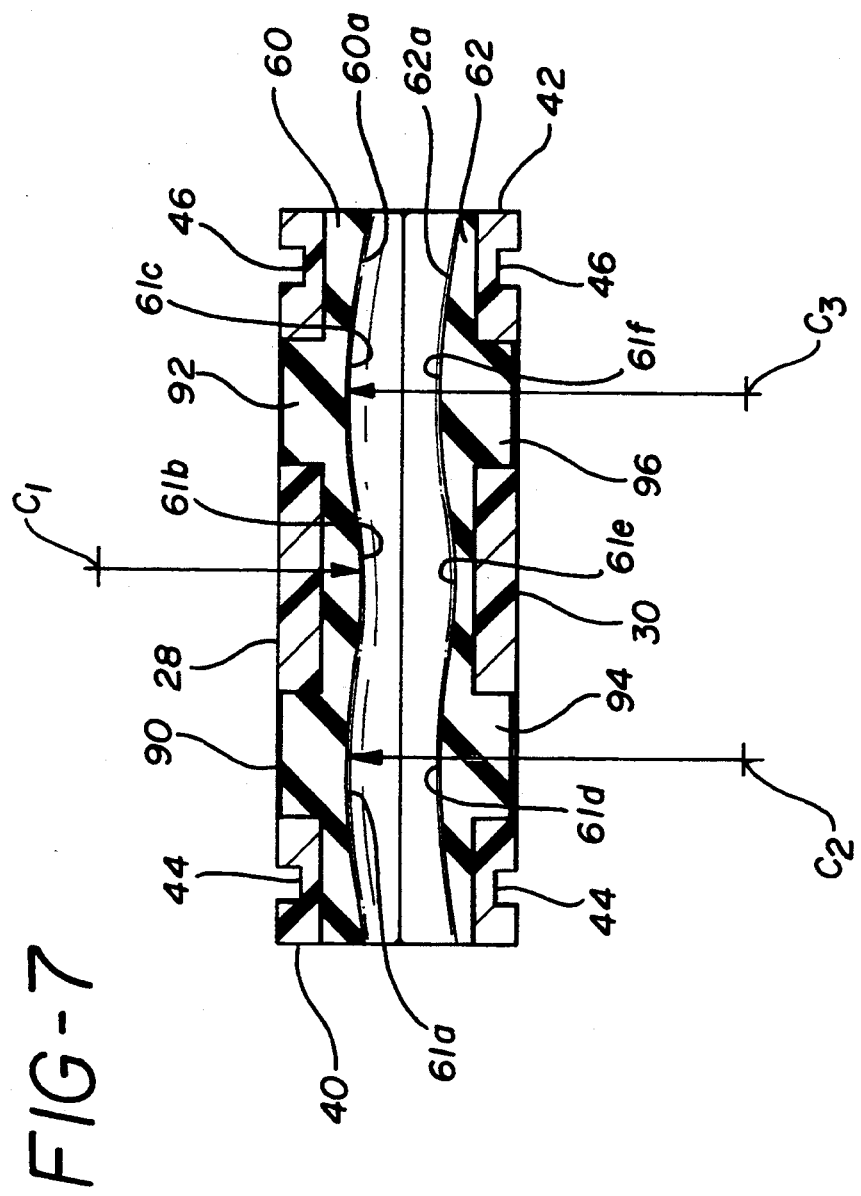
FIG. 7 is a cross-sectional view through section 7—7 showing the contour of the inside of the liner.
Figure 8:
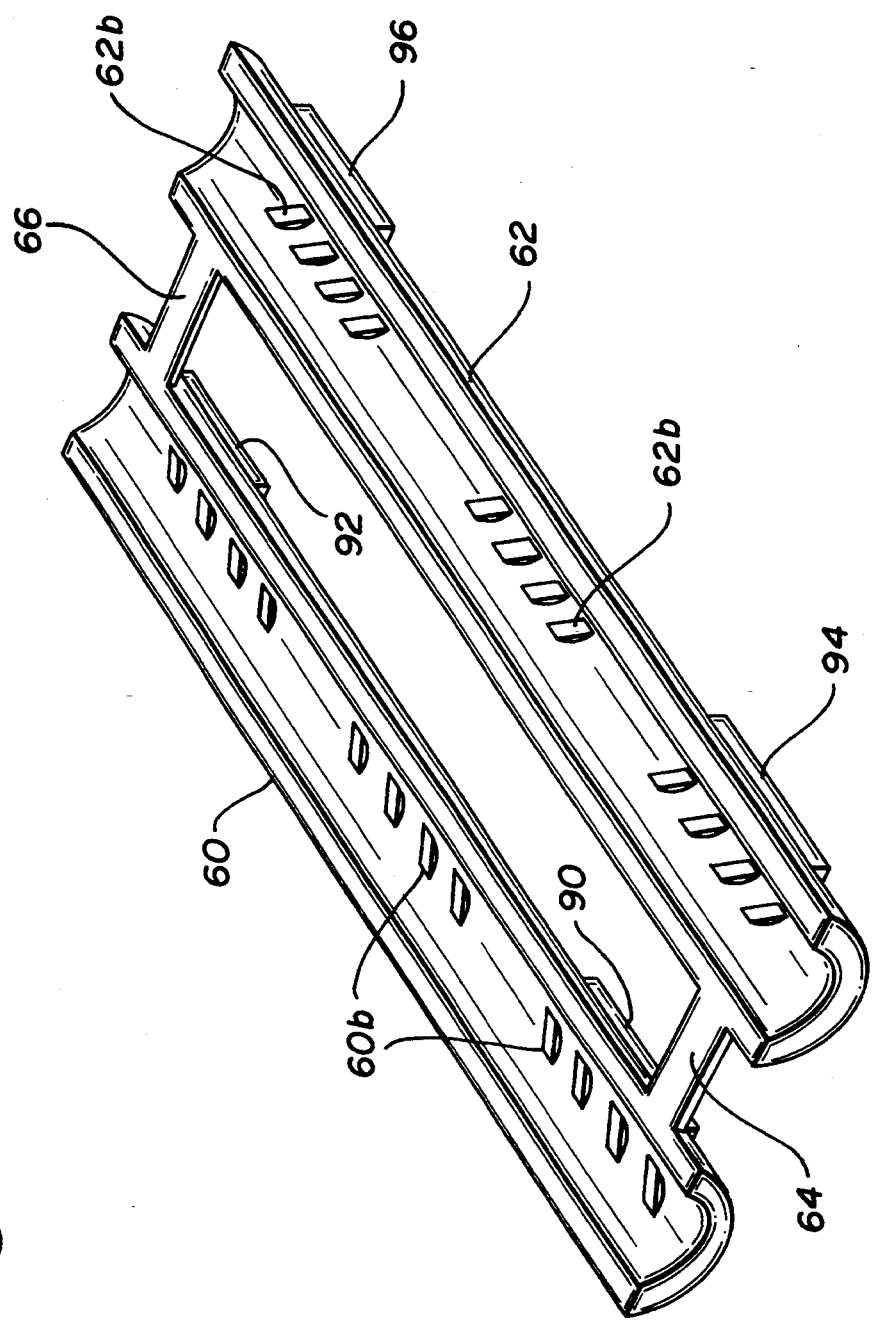
FIG. 8 is a top perspective view of an alternate embodiment of the liner of the invention.

The inner surfaces 60a and 62a of liners 60 and 62 are contoured so that if an axial pulling force is applied to tubing 12 a component of that force will be directed at an acute angle to the axial force. Although many contours will provide this effect, a generally sinusoidal contour 78 is preferred as shown in FIG. 7. The contour of surface 60a shown in FIG. 7 corresponds with the curvature of three circles. Surface 61b corresponds with an arc of the circumference of a circle whose center point is located at a point $C_1$, outside tube holder 38 and half way along the length of tube holder 38. Surfaces 61a and 61c correspond to an arc of the circumference of circles whose center points are respectively located at points $C_2$ and $C_3$ and respectively one third of the length of tube holder 38 from the ends of tube holder 38. Surfaces 61d, e and f are similarly contoured to be parallel to surfaces 61a, b and c. A similar effect may be achieved by providing the liners 60 and 62 with protrusions such as ribs or studs 60b and 62b as shown in FIG. 8.

It is possible though not preferred to omit liners 60 and 62. In such an embodiment, as shown in FIG. 8, the inner surfaces of grippers 28 and 30 may be contoured or may be provided with ribs or similar protrusions 78a as shown in FIG. 9.

The fixation device 10 is used by simply placing the tubing longitudinally in one of liners 60 or 62 and closing the fastener by bringing tabs 24 and 26 together. The tabs are releasably fastened to each other by means of snap-connector 22. Thereafter, the fastener is secured to the patient by placing the fin 20 flat on skin 36 and suturing fin 20 to the skin using holes 32 and/or 34. The tubing may be removed by un-snapping connector 22 by grasping overlapping portions 48 and 50. The fixation device is made by conventional injection molding techniques.

We claim:

1. A medical device for securing tubing to a patient, the device comprising:

a first elongate semi-cylindrical member and a second elongate semi-cylindrical member, the first and second members respectively comprising first and second elongate gripping channels and first and second tabs secured respectively to first and second gripping channels, the first and second tabs respectively lying lengthwise substantially parallel to the first and second elongate gripping channels, at least one of the gripping channels being provided with an inner gripping surface comprising gripping means for gripping the tubing, the gripping means comprising a tacky material;

connecting means for releasably connecting the tabs, said connecting means comprising a first fitting on said first member and a second fitting on said second member, said fittings releasably engaging upon closure of the members and the tabs touch each other, and the tubing is gripped between the first and second elongate gripping channels.

2. The device of claim 1 further comprising a hinge disposed between the first and second members and about which the members can rotate between an open position and the closed position.

3. The device of claim 2 wherein each elongate gripping channel comprises a tab edge and a hinge edge, the first and second tabs being respectively secured to the tab edges of the first and second elongate gripping channels and the hinge being secured to the first and second elongate gripping channels at their hinge edges.

4. The device of claim 1 wherein the connecting means comprises connector means for releasably joining the first and second tabs when the semi-cylindrical members are in the closed position.

5. The device of claim 1 wherein the first tab comprises a first overlapping portion which overlaps the second tab when the semi-cylindrical members are in the closed position.

6. The device of claim 5 wherein a suture hole is provided in the first overlapping portion.

7. The device of claim 1 wherein the second tab comprises a second overlapping portion which overlaps the first tab when the semi-cylindrical members are in the closed position.

8. The device of claim 7 wherein a suture hole is provided in the second overlapping portion.

9. The device of claim 1 wherein at least one of the tabs is provided with a suture hole.

10. The device of claim 1 wherein the gripping means comprise a contoured surface.

11. The device of claim 1 wherein the gripping means comprise an uneven surface.

12. The device of claim 1 wherein the gripping means comprise a generally sinusoidal surface.

13. The device of claim 1 wherein the gripping surface means comprise a toughened surface.

14. The device of claim 1 wherein the gripping means comprise a plurality of bumps.

15. The device of claim 1 wherein the gripping means comprise a liner, the liner comprising a tacky gripping surface.

16. The device of claim 15 wherein the liner comprises an uneven gripping surface.

17. The device of claim 15 wherein the liner comprises a contoured gripping surface.

18. The device of claim 17 wherein the contoured surface is generally sinusoidal.

19. The device of claim 17 wherein the contoured surface is roughened.

20. The device of claim 17 wherein the contoured surface comprises a plurality of bumps.

21. A medical device for securing tubing to a patient, the device comprising:
- a first semi-cylindrical member and a second semi-cylindrical member, the first and second semi-cylindrical members respectively comprising first and second elongate gripping channels and first and second tabs respectively secured to the first and second elongate gripping channels;
- a hinge disposed between the first and second semi-cylindrical members and secured to the first and second elongate gripping channels such that the semi-cylindrical members are rotatable about the hinge between an open position and a closed position in which the tubing is gripped between the elongate gripping channels;
- a connector for releasably connecting the first semi-cylindrical member to the second semi-cylindrical member comprising a first fitting on said first, member and a second fitting on said second member, said fittings releasably engaging when the device is in the closed position; and
- liner means disposed in the first and second elongate gripping channels, the liner comprising a tacky surface to grip the tubing.

22. The device of claim 21 wherein the liner comprises a contoured surface.

23. The device of claim 22 wherein the contoured surface is generally sinusoidal.

24. The device of claim 22 wherein the contoured surface comprises a plurality of bumps.

25. The device of claim 22 wherein the contoured surface is roughened.

26. The device of claim 21 wherein the liner comprises an uneven gripping surface.

27. The device of claim 21 wherein the liner comprises a roughened surface.

* * * * *